(12) United States Patent  
Lim (10) Patent No.: US 6,390,843 B1
(45) Date of Patent: May 21, 2002

(54) LEAD LOCK FOR IMPLANTABLE MEDICAL DEVICE

(75) Inventor: Wisit Lim, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/887,811

(22) Filed: Jun. 22, 2001

(51) Int. Cl.[7] ............................................... H01R 4/50
(52) U.S. Cl. ...................... 439/346; 439/904; 439/349; 607/37
(58) Field of Search .............................. 439/346, 909, 439/349, 350, 371, 372, 359, 725, 668; 607/37, 38, 36

(56) References Cited

U.S. PATENT DOCUMENTS

| | | | |
|---|---|---|---|
| 4,540,236 A | 9/1985 | Peers-Trevarton | 339/45 R |
| 4,712,557 A | 12/1987 | Harris | 128/419 P |
| 4,715,380 A | 12/1987 | Harris | 128/419 P |
| 4,860,750 A | 8/1989 | Frey et al. | 128/419 P |
| 5,007,864 A | 4/1991 | Stutz, Jr. | 439/651 |
| 5,252,090 A | 10/1993 | Giurtino et al. | 439/441 |
| 5,261,395 A | 11/1993 | Oleen et al. | 607/15 |
| 5,413,595 A | 5/1995 | Stutz, Jr. | 607/637 |
| 5,486,202 A * | 1/1996 | Bradshaw | 607/37 |
| 5,509,928 A | 4/1996 | Acken | 607/37 |
| 5,766,042 A * | 6/1998 | Ries et al. | 439/668 |
| 5,951,595 A | 9/1999 | Moberg et al. | 607/37 |
| 5,989,077 A * | 11/1999 | Mast et al. | 439/814 |
| 6,029,089 A * | 2/2000 | Hawkins et al. | 607/37 |
| 6,080,188 A * | 6/2000 | Rowley et al. | 607/37 |
| 6,192,277 B1 * | 2/2001 | Lim et al. | 607/37 |
| 6,312,297 B1 * | 11/2001 | Lorkowski | 439/838 |

* cited by examiner

Primary Examiner—P. Austin Bradley
Assistant Examiner—Ross Gushi (57) ABSTRACT

A connector system for use with a sealed implantable medical device having a lead receiving channel for slidably receiving a connecting end of an electrical lead includes an entrance block attached to the medical device and having an inlet bore for reception of the electrical lead. A clamp assembly within the entrance block includes a mounting member and a unitary cylindrically shaped loop clamp having an adjustable diameter. The loop clamp is coaxial with the inlet bore and movable between a first position firmly engaged with the electrical lead received in the inlet bore so as to prevent withdrawal of the electrical lead from the inlet bore and a second position disengaged from the electrical lead and freely permitting withdrawal of the electrical lead from the inlet bore. An actuator mechanism is operable for shifting the loop clamp between the first and second positions.

16 Claims, 5 Drawing Sheets

LEAD LOCK FOR IMPLANTABLE MEDICAL DEVICE

FIELD OF THE INVENTION

The present invention relates generally to an electrical connector system for use with an implantable medical device such as a pacemaker for connecting an implantable electrical lead to the electrical circuits contained within a hermetically sealed housing of the medical device.

BACKGROUND OF THE INVENTION

While the present invention will be described in a specific manner as being applicable to a pacemaker, it will be understood that the invention is applicable to any other type of implantable medical device intended to stimulate body tissue.

Modem pacemakers monitor the activity of a heart and provide a stimulation pulse in the absence of normal heart activity. Advantageously, such devices are relatively small, light-weight and implantable. In order to sense and stimulate the heart, however, such pacemakers must be used with a pacemaker lead, an electrical conductor that carries electrical signals between the heart and the pacemaker. Advantageously, the pacemaker lead can be inserted into the heart transvenously through a relatively simple and well-known surgical procedure. Disadvantageously, one end of the lead (designated herein as the "connecting end") must be electrically and mechanically secured to the pacemaker in a way that provides for a long-term safe and secure, yet detachable connection. Those skilled in the pacemaker art have long sought for a simple, yet reliable and safe, technique for making this detachable electrical and mechanical connection between the pacemaker device and the connecting end of the pacemaker lead.

Figure 1:
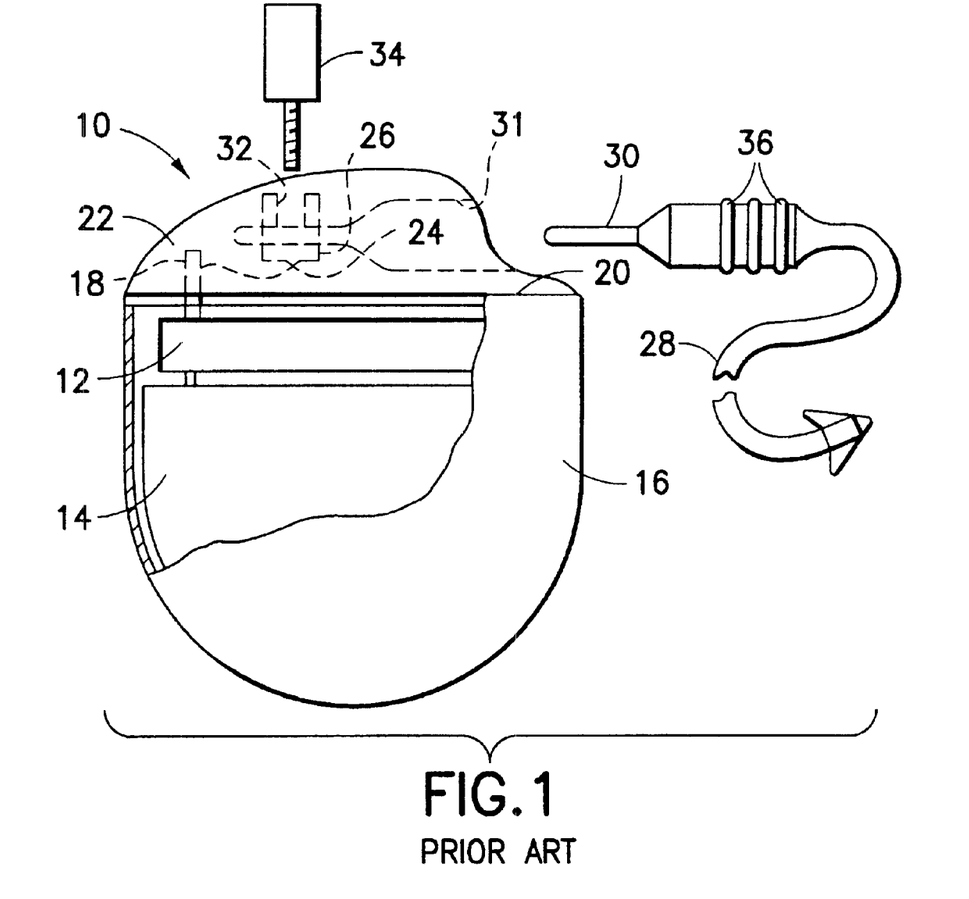
FIG. 1. is an exploded perspective view of a known pacemaker, illustrating a sealed pacemaker housing and its associated cast epoxy connector top, and an associated pacemaker lead ready for insertion into a receiving channel of the connector.

In order to appreciate the advantages of the present invention, it will help first to have a basic understanding of the manner in which the mechanical and electrical connection functions are carried out in known pacemakers. The main components associated with the connection function of such known pacemakers are shown diagrammatically in FIG. 1. A pacemaker 10 electrically includes a battery 14 that powers electrical circuits 12. The pacemaker electrical circuits 12 and battery 14 are mechanically enclosed and hermetically sealed in a suitable housing 16. Typically, this housing or case 16 is shaped to include a flat side or platform 20 to which a suitable epoxy connector 22 can be bonded. At least one feedthrough terminal, 18, in electrical contact with the electrical circuits 12, passes through the case or housing 16 and protrudes beyond the platform 20. This feedthrough terminal 18 is electrically isolated from the case 16. A platinum wire 24, or other suitable conductive element, connects the terminal 18 to a conductive connector block 26 that is fitted within the connector 22. A pacemaker lead 28, having a proximal electrode 30, connects to the pacemaker electrical circuits by inserting the proximal electrode 30 into a receiving channel 31 of the connector 22 until the electrode 30 is in contact with the connector block 26. A set screw 32 is then securely tightened using a torque wrench 34 to firmly hold the electrode 30 in both mechanical and electrical connection with the connector block 26. A septum, not shown but having the construction generally described in commonly assigned U.S. Pat. No. 5,509,928 issued Apr. 23, 1996 to Acken, is typically placed over the set screw 32 in order to prevent body fluids from seeping through the set screw hole. Further, sealing ribs or ridges 36 on the connecting end of the pacemaker lead are designed to tightly engage the inside edges of the receiving channel 31 in order to prevent any body fluids from entering into the receiving channel 31 once the connecting end of the lead has been inserted into the connector 22.

While the descriptions presented in the prior art vary greatly relative to, for example, different types of locking mechanisms for performing the mechanical connection function, or different types of arrangements for performing the electrical feedthrough function, including the use of bipolar or multiple pacemaker leads, all such systems include the use of a premolded or cast connector 22 that is bonded to a sealed pacemaker housing 16 in which the electrical circuits are located.

Typically, prior art connectors 22 are cast in place from epoxy to the platform or header 20 of the pacemaker, or a premolded connector is bonded to the platform 20 using a suitable sealing and bonding agent. Further, once the electrical connection is made from the terminal post 18 to the connector block 26, and the connector is attached to the housing, all remaining voids within the connector 22, not including the receiving channel 31 into which the proximal end of the pacemaker lead 28 is to be inserted, must be filled with a suitable filler material, such as a two-component epoxy or silicone rubber.

As is evident from the above description, placing a connector on a pacemaker housing is a very labor-intensive process involving many components. What is needed is a similar manner of lead attachment that provides the requisite mechanical and electrical connection functions using fewer components and less labor yet providing higher reliability. The present invention addresses these and other needs.

In a subsequent development, as disclosed in U.S. Pat. No. 5,951,595 issued Sep. 14, 1999 to Moberg et al., an active lock but passive release connector assembly includes an entrance block leading to lead receiving channels of an implantable medical device provided with two seals which, when compressed by the entrance block, lock onto the body of each lead. As one drawback of the Moberg et al. device, it periodically occurs that when the leads need to be extracted and the mechanism is released, causing the plunger to move back away from the seals, it sometimes occurs that the seals remain tightly locked onto the leads after the plunger is released from the seals. This requires a higher extraction force than should normally be necessary. In the present invention, in contrast, when the mechanism is loosened, the clamp is actively released from the lead body, enabling the lead to then be easily extracted from the device.

It was with knowledge of the foregoing state of the technology that the present invention has been conceived and is now reduced to practice.

SUMMARY OF THE INVENTION

A connector system for use with a sealed implantable medical device includes an entrance block attached to the medical device with an inlet bore for receiving an electrical lead such that, when attached to the medical device, the inlet bore is coaxial with the lead receiving channel of the medical device. A clamp assembly within the entrance block includes a mounting member, a cylindrically shaped loop clamp unitary with the mounting member having an adjustable diameter, the loop clamp being coaxial with the inlet bore and movable between a first position disengaged from the electrical lead and freely permitting withdrawal of the electrical lead from the inlet bore and a second position firmly engaged with the electrical lead received in the inlet bore so as to prevent its withdrawal from the inlet bore, and an actuator mechanism for shifting the loop clamp between the first and second positions.

In a preferred design the connector system is intended for use with an implantable medical device having a pair of lead receiving channels while incorporating all of the features of the single lead receiving channel design.

It is a feature of the present invention to provide an electrical connector system for use with an implantable medical device such as a pacemaker for connecting an implantable electrical lead to the electrical circuits contained within a hermetically sealed housing of the medical device.

It is a further feature of the present invention to provide such an electrical connector system which enables the electrical leads to be readily selectively firmly attached to the medical device in one instance and just as readily detached in another instance.

Still a further feature of the present invention is to provide such an electrical connector which includes an entrance block attached to the medical device and having an inlet bore for reception therethrough of the electrical lead and, when positioned for attachment to the medical device, the inlet bore being coaxial with the lead receiving channel, a clamp assembly within the entrance block including a mounting member, a cylindrically shaped loop clamp unitary with the mounting member having an adjustable diameter, the loop clamp being coaxial with the inlet bore and movable between a first position disengaged from the electrical lead and freely permitting withdrawal of the electrical lead from the inlet bore and a second position firmly engaged with the electrical lead received in the inlet bore so as to prevent its withdrawal from the inlet bore, and an actuator mechanism for shifting the loop clamp between the first and second positions.

Yet a further feature of the present invention is to provide such an electrode assembly with a construction which activates with a special driver stylet A still further feature of the present invention is to provide such an electrical connector in which the entrance block includes first and second opposed spaced apart side walls, with a first retainer bore in the first side wall extending transverse of the inlet bore and a second retainer bore in the second side wall generally aligned with the first retainer bore, in which the actuator mechanism includes an actuator block with a threaded bore therein aligned with the first and second retainer bores, an actuating screw having a head rotatably received in the first retainer bore, being threadedly engaged with the threaded bore of the actuator block, and extending to a terminal journal rotatably received in the second retainer bore and in which the loop clamp extends between a first end at the mounting member and a second end fixed to the actuator block, whereby rotation of the actuating screw in one direction shifts the loop clamp from the first position to the second position and whereby rotation of the actuating screw in the opposite direction shifts the loop clamp from the second position to the first position.

Yet another feature of the present invention is to provide such an electrical connector which includes an annular seal received in the inlet bore of the entrance block adjacent the clamp assembly, the annular seal being coaxial and aligned with the inlet bore for sealing engagement with the electrical lead when the electrical lead is received in the inlet bore.

Yet a further feature of the present invention is to provide such an electrical connector according to which the annular seal has an inner peripheral surface and at least one rim member projecting inwardly from the inner peripheral surface, the rim member being sealingly engaged with the electrical lead when the electrical lead is received in the inlet bore.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 2:
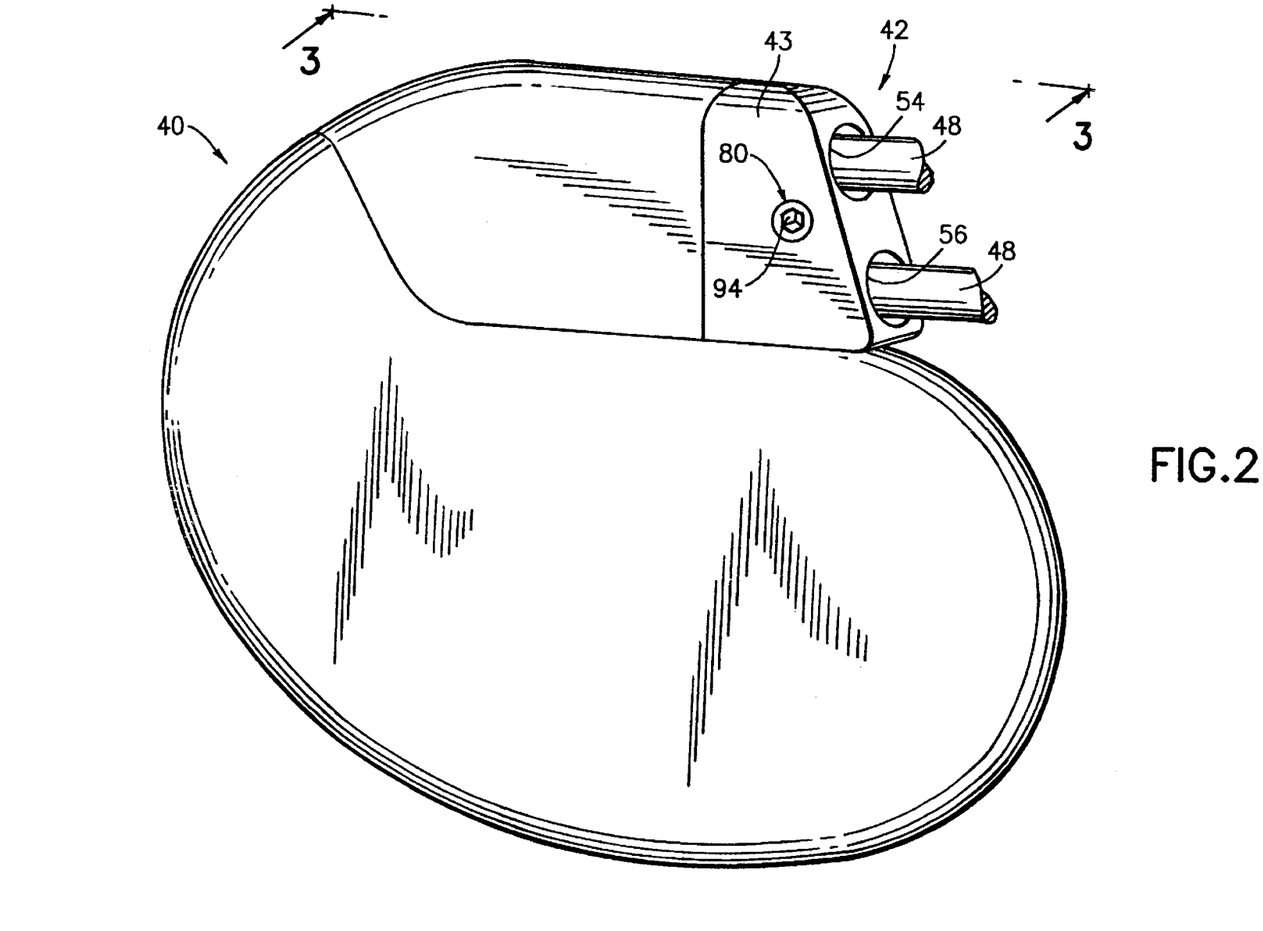
FIG. 2. is a perspective view of a pacemaker embodying the present invention.

Turn now to the drawings and, initially now to FIG. 2 which generally illustrates a perspective view of a sealed implantable medical device, a cardiac stimulation device such as a pacemaker 40 and an associated connector system 42. Although the present invention will be described with reference to the embodiments shown in the drawings, it should be understood that the present invention can be embodied in many alternate forms or embodiments. In addition, any suitable size, shape or type of elements or materials may be used.

The connector system 42 used with the sealed implantable medical device 40 includes an entrance block 43, typically of polysulfone and suitably attached to the medical device in any known manner. For example, it may be attached by way of a tongue-and-groove construction as generally indicated by reference numeral 143 in FIGS. 3, 4, and 5A. The medical device 40 has first and second lead receiving channels, 44, 46 (FIG. 3), each for slidably receiving a connecting end of an electrical lead 48, and each lead receiving channel has an open end 50 for receiving its associated electrical lead and a closed end 52. The entrance block 43 typically has first and second inlet bores 54, 56 for reception therethrough of its associated electrical lead and, when positioned for attachment to the medical device, the inlet bores 54, 56 are coaxial with their associated lead receiving channels 44, 46.

As seen in FIGS. 3, 4, 5, and 6, a clamp assembly 58 is provided within the entrance block 43. The clamp assembly 58 includes a mounting member 60 and first and second cylindrically shaped loop clamps 62, 64 which are unitary with the mounting member. The clamp assembly may be fashioned from a thin strip of any suitable biocompatible sheet material and must have some degree of resiliency. When received in the entrance block 43, each of the loop clamps 62, 64 has an adjustable diameter, the first loop clamp being coaxial with the first inlet bore 54, the second loop clamp being coaxial with the second inlet bore 56. Each loop clamp 62, 64 is movable between a first position firmly engaged with its associated electrical lead 48 (see dashed line representation in FIG. 5) so as to prevent withdrawal of each electrical lead from its associated inlet bore 54, 56 and a second position (see solid line representation in FIG. 5) disengaged from the electrical lead and freely permitting withdrawal of the electrical lead from its associated inlet bore.

Figures 5, 5A:
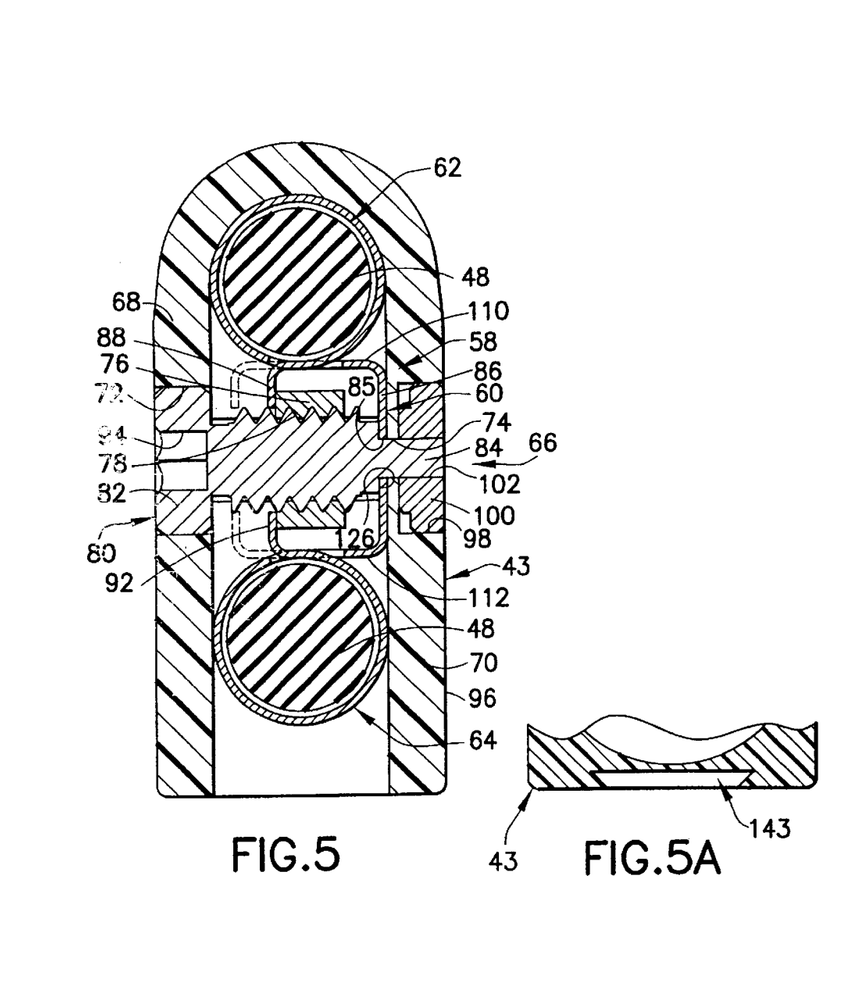
FIG. 5 is a cross-section view taken generally along line 5—5 in FIG. 4.
FIG. 5A is a detail cross-section view taken generally along line 5A—5A in FIG. 4.

An actuator mechanism 66 serves to shift the first and second loop clamps 62, 64 between the first and second positions. The entrance block 43 includes first and second opposed spaced apart side walls 68, 70, with a first retainer bore 72 in the first side wall 68 extending transverse of the inlet bores 54, 56 and a second retainer bore 74 in the second side wall 70 generally aligned with the first retainer bore. The actuator mechanism 66 includes an actuator block 76 with a threaded bore 78 therein aligned with the retainer bores 72, 74. An actuating screw 80 is rotatably received at its opposite ends 82, 84 in the retainer bores 72, 74, respectively, extends through an aperture 85 in the mounting member 60, and is threadedly engaged with the threaded bore 78 of the actuator block 76.

Figure 6:
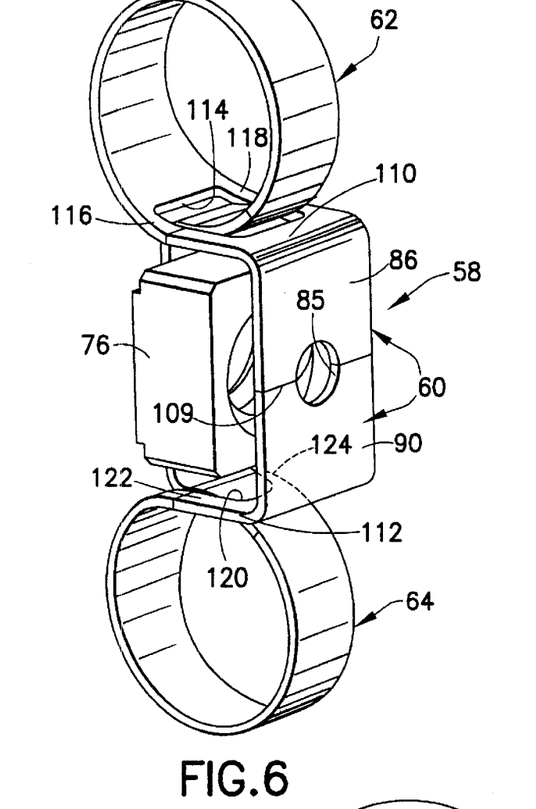
FIG. 6 is a perspective view of a component illustrated in FIGS. 3, 4, and 5.
Figure 7:
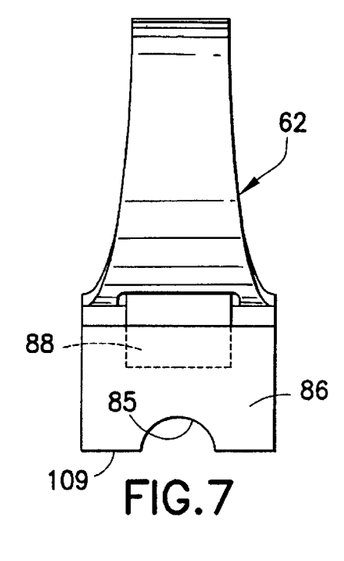
FIG. 7 is a front elevation view of a portion of FIG. 6.
Figure 8:
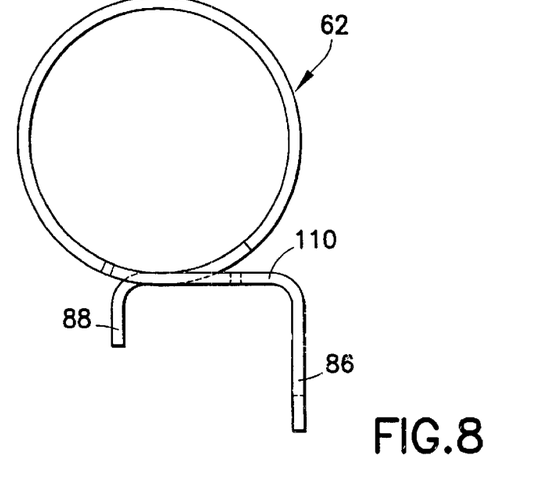
FIG. 8 is a side elevation view of the component illustrated in FIG. 7.

As seen especially well in FIGS. 5 and 6, the first loop clamp 62 extends between a first end 86 at the mounting member 60 and a second end 88 fixed to the actuator block 76. Similarly, the second loop clamp 64 extends between a first end 90 at the mounting member 60 and a second end 92 fixed to the actuator block. With this construction, rotation of the actuating screw 80 effected in one direction shifts each of the first and second loop clamps 62, 64 from the first position (solid line representation in FIG. 5) to the second position (dashed line representation in FIG. 5) and rotation of the actuating screw in the opposite direction shifts each of the first and second loop clamps from the second position to the first position. Indeed, such operation of the actuating screw 80 may be effected by means of a hex wrench inserted into a hex receptacle 94 in the head end 82 within the retainer bore 72.

The second side wall 70 has an outer surface 96 with a cylindrical recess 98 coaxial with and of greater diameter than the second retainer bore 74. A retainer disk 100 having a central bore 102 extending therethrough is mounted in the cylindrical recess 98 and affixed to the second side wall 70 of the entrance block 43. The central bore 102 is aligned with the second retainer bore 74 and the terminal journal 84 of the actuating screw 80 is rotatably received in the central bore.

Figure 3:
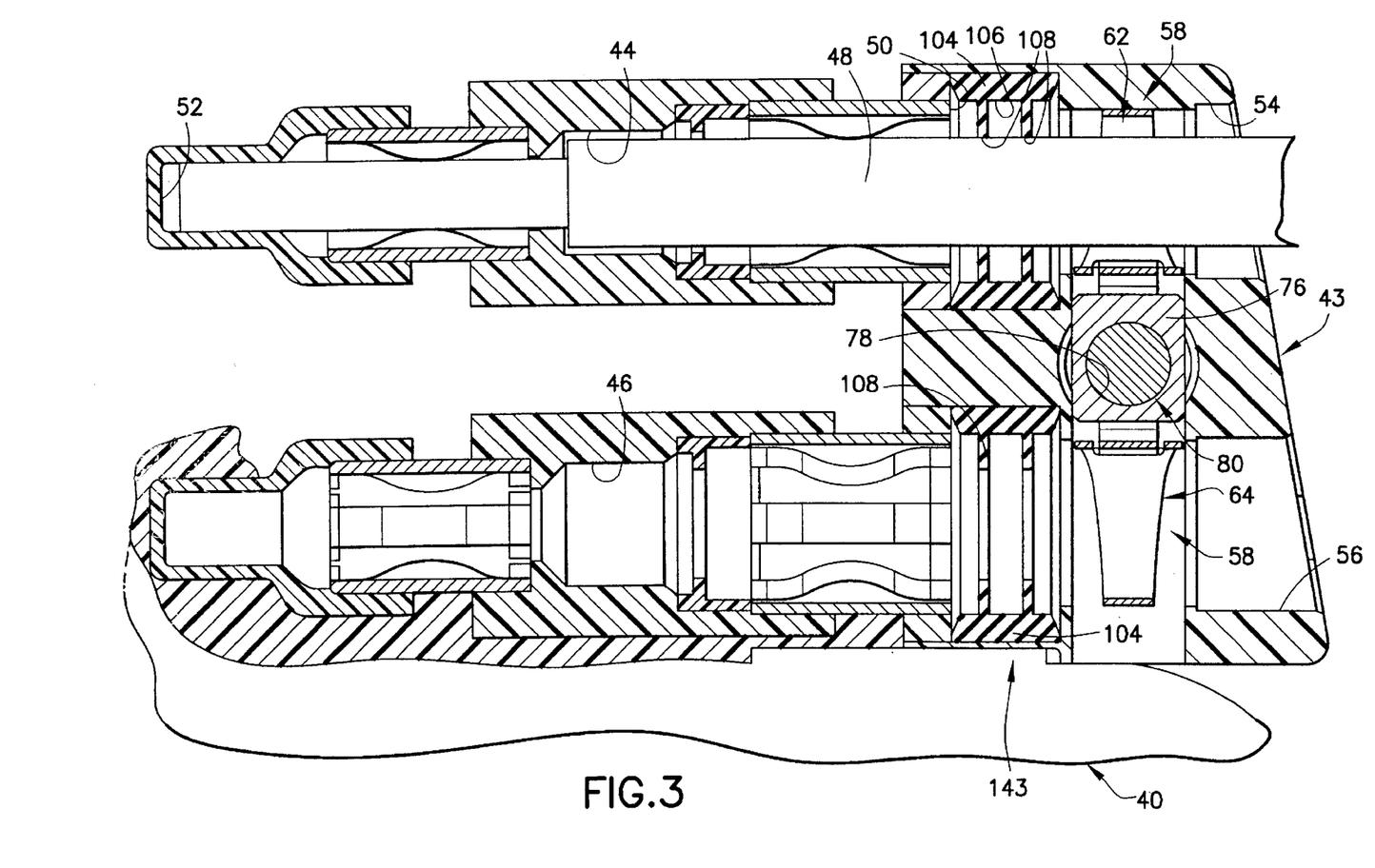
FIG. 3 is a cross-section view taken generally along line 3—3 in FIG. 2.
Figure 4:
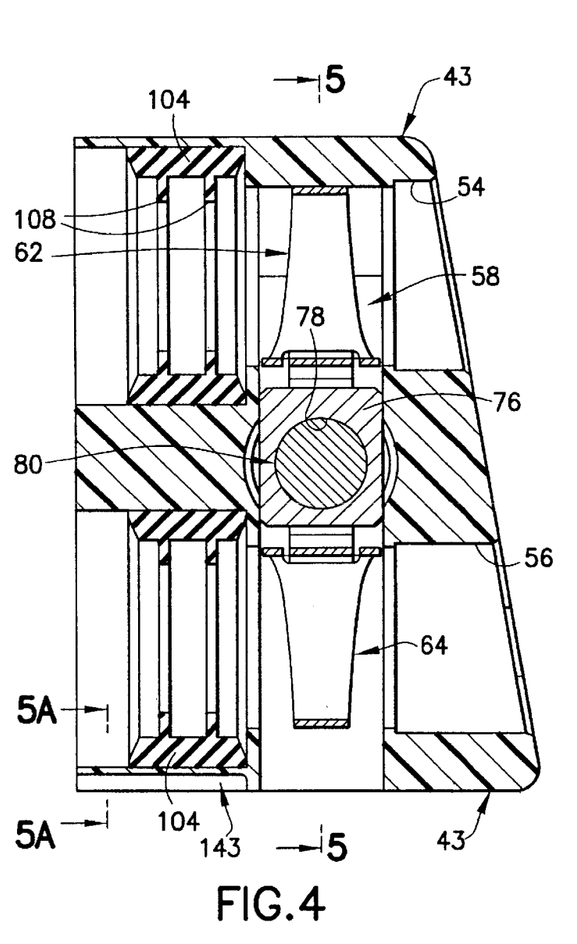
FIG. 4 is a detail cross-section view of a component illustrated in FIG. 3.

Viewing FIG. 3, an annular seal 104 is received in each of the first and second inlet bores 54, 56 of the entrance block 43 adjacent the clamp assembly 58. Each annular seal 104 is coaxial and aligned with its associated inlet bore for sealing engagement with its associated electrical lead 48 when that lead is received in the inlet bore. Additionally, each annular seal 104 has an inner peripheral surface 106 and at least one rim member 108 projecting inwardly from the inner peripheral surface. It is actually the rim member 108, which is sealingly engaged with the electrical lead.

Returning to a discussion of the clamp assembly 58, and with particular reference to FIGS. 5–8, it is seen that the mounting member 60 is generally unshaped including a bight portion, actually the adjacent ends 86, 90 of loop clamps 62, 64, respectively, which are suitably joined together along a joint line 109. The separate construction of the loop clamps 62, 64 assures manufacturing simplicity. Of course, the invention encompasses the use of only one loop clamp in the event the entrance block only accommodates one electrical lead. This bight portion is seen in FIG. 5 to be in contiguous engagement with the second side wall 70. Then, first and second generally parallel spaced apart leg members 110, 112 project away from the bight portion toward the first side wall 68. The first loop clamp 62 is actually an extension of the first leg member 110 and the second loop clamp 64 is actually an extension of the second leg member 112.

Viewing especially FIG. 6, the first leg member 110 has a central window section 114 defining first and second spaced apart fingers 116, 118 extending toward the first side wall 68 (FIG. 5). The first loop clamp 62 has a narrowed region extending through the central window section 114 between the first and second fingers 116, 118 and continuing to the second end 88 fixed to the actuator block 76. In a similar fashion, the second leg member 112 has a central window section 120 defining third and fourth spaced apart fingers 122, 124 extending toward the first side wall. Again, the second loop clamp 64 has a narrowed region extending through the central window section 120 between the third and fourth fingers 122, 124 and continuing to the second end 92 fixed to the actuator block.

The mounting member 60 and the first and second loop clamps 62, 64 are all composed of sheet material of substantially uniform thickness with spring tendency, that is, with a bias to return to an original orientation when moved to a different orientation. Also, each of the first and second loop clamps 62, 64 is of a generally uniform width but tapers to an enlarged width at its associated first end, 86 or 90. Further, each of the first and second leg members 110, 112 is of a generally uniform width which is greater than the uniform width portions of the first and second loop clamps 62, 64. The enlarged width portions of the first ends 86, 90 of the first and second loop clamps 62, 64, respectively, are substantially similar in width to the first and second leg members 110, 112. At the same time, the width of the second end 88 of the first loop clamp 62 is smaller than that of the central window section 114 in the first leg member 110 and the width of the second end 92 of the second loop clamp 64 is smaller than that of the central window section 120 in the second leg member 90.

With renewed attention to FIG. 5, it is seen that the actuating screw 80 has a transverse shoulder 126 adjacent the terminal journal 84 engaged with the bight portion of the mounting member 60 to maintain the bight portion and the mounting member in contiguous engagement with the second side wall 70.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A connector system for use with a sealed implantable medical device having a lead receiving channel for slidably receiving a connecting end of an electrical lead, the lead receiving channel having an open end for receiving the electrical lead and a closed end, the connector system comprising:

an entrance block attached to the medical device and having an inlet bore for reception therethrough of the electrical lead and, when positioned for attachment to the medical device, the inlet bore being coaxial with the lead receiving channel; and a clamp assembly within the entrance block including:
a mounting member;
a cylindrically shaped loop clamp unitary with the mounting member having an adjustable diameter, the loop clamp being coaxial with the inlet bore and movable between a first position disengaged from the electrical lead and freely permitting withdrawal of the electrical lead from the inlet bore and a second position firmly engaged with the electrical lead received in the inlet bore so as to prevent withdrawal of the electrical lead from the inlet bore; and
an actuator mechanism for shifting the loop clamp between the first and second positions.

2. A connector system as set forth in claim 1:
wherein the entrance block has a retainer bore extending transverse of the inlet bore;
wherein the actuator mechanism includes:
an actuator block with a threaded bore therein aligned with the retainer bore; and
an actuating screw rotatably received in the retainer bore and threadedly engaged with the threaded bore of the actuator block;
wherein the loop clamp extends between a first end at the mounting member and a second end fixed to the actuator block;
whereby rotation of the actuating screw in one direction shifts the loop clamp from the first position to the second position; and
whereby rotation of the actuating screw in the opposite direction shifts the loop clamp from the second position to the first position.

3. A connector system as set forth in claim 1 including:
wherein the entrance block includes first and second opposed spaced apart side walls, with a first retainer bore in the first side wall extending transverse of the inlet bore and a second retainer bore in the second side wall generally aligned with the first retainer bore;
wherein the actuator mechanism includes:
an actuator block with a threaded bore therein aligned with the first and second retainer bores;
an actuating screw having a head rotatably received in the first retainer bore, being threadedly engaged with the threaded bore of the actuator block, and extending to a terminal journal rotatably received in the second retainer bore;
wherein the loop clamp extends between a first end at the mounting member and a second end fixed to the actuator block;
whereby rotation of the actuating screw in one direction shifts the loop clamp from the first position to the second position; and
whereby rotation of the actuating screw in the opposite direction shifts the loop clamp from the second position to the first position.

4. A connector system as set forth in claim 3:
wherein the second side wall has an outer surface with an cylindrical recess coaxial with and of greater diameter than the second retainer bore; and
a retainer disk having a central bore mounted in the cylindrical recess of the second side wall, the central bore being aligned with the second retainer bore, the terminal journal of the actuating screw being rotatably received in the central bore of the retainer disk.

5. A connector system as set forth in claim 3 including:
an annular seal received in the inlet bore of the entrance block adjacent the clamp assembly, the annular seal being coaxial and aligned with the inlet bore for sealing engagement with the electrical lead when the electrical lead is received in the inlet bore.

6. A connector system as set forth in claim 5:
wherein the annular seal has an inner peripheral surface and at least one rim member projecting inwardly from the inner peripheral surface, the rim member being sealingly engaged with the electrical lead when the electrical lead is received in the inlet bore.

7. A connector system for use with a sealed implantable medical device having first and second lead receiving channels, each for slidably receiving a connecting end of an electrical lead, each lead receiving channel having an open end for receiving its associated electrical lead and a closed end, the connector system comprising:
an entrance block attached to the medical device and having first and second inlet bores for reception therethrough of its associated electrical lead and, when positioned for attachment to the medical device, the inlet bores being coaxial with their associated lead receiving channels;
a clamp assembly within the entrance block including:
a mounting member;
first and second cylindrically shaped loop clamps unitary with the mounting member, each of the loop clamps having an adjustable diameter, the first loop clamp being coaxial with the first inlet bore, the second loop clamp being coaxial with the second inlet bore, each loop clamp being movable between a first position disengaged from the electrical lead and freely permitting withdrawal of the electrical lead from its associated inlet bore and a second position firmly engaged with its associated electrical lead so as to prevent withdrawal of the electrical lead from its associated inlet bore; and
an actuator mechanism for shifting the first and second loop clamps between the first and second positions.

8. A connector system as set forth in claim 7:
wherein the entrance block has a retainer bore extending transverse of the first and second inlet bores;
wherein the actuator mechanism includes:
an actuator block with a threaded bore therein aligned with the retainer bore; and
an actuating screw rotatably received in the retainer bore and threadedly engaged with the threaded bore of the actuator block;
wherein the first loop clamp extends between a first end at the mounting member and a second end fixed to the actuator block;
wherein the second loop clamp extends between a first end at the mounting member and a second end fixed to the actuator block;
whereby rotation of the actuating screw in one direction shifts each of the first and second loop clamps from the first position to the second position; and
whereby rotation of the actuating screw in the opposite direction shifts each of the first and second loop clamps from the second position to the first position.

9. A connector system as set forth in claim 7 including:
wherein the entrance block includes first and second opposed spaced apart side walls, with a first retainer bore in the first side wall extending transverse of the inlet bore and a second retainer bore in the second side wall generally aligned with the first retainer bore:

wherein the actuator mechanism includes:

an actuator block with a threaded bore therein aligned with the first and second retainer bores; and an actuating screw having a head rotatably received in the first retainer bore, being threadedly engaged with the threaded bore of the actuator block, and extending to a terminal journal rotatably received in the second retainer bore;

wherein the first loop clamp extends between a first end at the mounting member and a second end fixed to the actuator block;

wherein the second loop clamp extends between a first end at the mounting member and a second end fixed to the actuator block;

whereby rotation of the actuating screw in one direction shifts each of the first and second loop clamps from the first position to the second position; and whereby rotation of the actuating screw in the opposite direction shifts each of the first and second loop clamps from the second position to the first position.

10. A connector system as set forth in claim 9:

wherein the second side wall has an outer surface with a cylindrical recess coaxial with and of greater diameter than the second retainer bore; and a retainer disk having a central bore mounted in the cylindrical recess of the second side wall, the central bore being aligned with the second retainer bore, the terminal journal of the actuating screw being rotatably received in the central bore of the retainer disk.

11. A connector system as set forth in claim 9 including:

an annular seal received in each of the first and second inlet bores of the entrance block adjacent the clamp assembly, each annular seal being coaxial and aligned with its associated inlet bore for sealing engagement with its associated electrical lead when the associated electrical lead is received in the inlet bore.

12. A connector system as set forth in claim 11:

wherein each annular seal has an inner peripheral surface and at least one rim member projecting inwardly from the inner peripheral surface, the rim member being sealingly engaged with its associated electrical lead when the electrical lead is received in the inlet bore.

13. A connector system as set forth in claim 9:

wherein the mounting member is generally u-shaped including a bight portion in contiguous engagement with the second side wall and first and second generally parallel spaced apart leg members projecting away from the bight portion toward the first side wall, the first loop clamp being an extension of the first leg member, the second loop clamp being an extension of the second leg member.

14. A connector system as set forth in claim 13:

wherein the actuating screw has a transverse shoulder adjacent the terminal journal engaged with the bight portion to maintain the bight portion in contiguous engagement with the second side wall.

15. A connector system as set forth in claim 13:

wherein the first leg member has a central window section defining first and second spaced apart fingers extending toward the first side wall, the first loop clamp having a narrowed region extending through the central window section between the first and second fingers and continuing to the second end fixed to the actuator block; and wherein the second leg member has a central window section defining third and fourth spaced apart fingers extending toward the first side wall, the second loop clamp having a narrowed region extending through the central window section between the third and fourth fingers and continuing to the second end fixed to the actuator block.

16. A connector system as set forth in claim 15:

wherein the mounting member and the first and second loop clamps are all composed of sheet material of substantially uniform thickness;

wherein each of the first and second loop clamps is generally of a substantially uniform width but tapering to an enlarged width at their first ends, respectively;

wherein each of the first and second leg members is of a substantially uniform width greater than that of the substantially uniform width portions of the first and second loop clamps, the enlarged width portions of the first ends of the first and second loop clamps being substantially similar in width to the first and second leg members, respectively;

wherein the width of the second end of the first loop clamp is smaller than that of the central window section in the first leg member; and wherein the width of the second end of the second loop clamp is smaller than that of the central window section in the second leg member.

* * * * *